United States Patent [19]

Sciavolino

[11] 4,150,220

[45] Apr. 17, 1979

[54] SEMI-SYNTHETIC 4"-ERYTHROMYCIN A DERIVATIVES

[75] Inventor: Frank C. Sciavolino, East Lyme, Conn.

[73] Assignee: Pfizer Inc., New York, N.Y.

[21] Appl. No.: 856,479

[22] Filed: Dec. 1, 1977

Related U.S. Application Data

[63] Continuation-in-part of Ser. No. 765,480, Feb. 4, 1977, abandoned.

[51] Int. Cl.$^2$ ...................... C07H 17/08; A61K 31/70
[52] U.S. Cl. .......................................... 536/9; 536/17; 424/180
[58] Field of Search ............................ 536/9; 260/343

[56] References Cited

U.S. PATENT DOCUMENTS

| | | | |
|---|---|---|---|
| 3,842,069 | 10/1974 | Jones | 536/9 |
| 3,884,903 | 5/1975 | Jones | 536/9 |

OTHER PUBLICATIONS

Chemical Abstracts, 84, 1976, 121360k.

*Primary Examiner*—Johnnie R. Brown
*Assistant Examiner*—Blondel Hazel
*Attorney, Agent, or Firm*—Francis X. Murphy; Charles J. Knuth; Albert E. Frost

[57] ABSTRACT

A series of 4"-deoxy-4"-amino-erythromycin A antibacterial agents and their preparation from erythromycin A via 4"-deoxy-4"-oxo-erythromycin A intermediates.

19 Claims, No Drawings

SEMI-SYNTHETIC 4"-ERYTHROMYCIN A DERIVATIVES

CROSS-REFERENCE TO RELATED APPLICATIONS

This application is a continuation-in-part of co-pending application Ser. No. 765,480, filed Feb. 4, 1977, and now abandoned.

BACKGROUND OF THE INVENTION

1. Field of the Invention

This invention relates to novel antibacterial agents, the intermediates leading thereto and processes for the preparation of said intermediates. In particular, the invention concerns 4"-deoxy-4"-amino-erythromycin A antibacterial agents, 4"-deoxy-4"-oxo-erythromycin A derivatives as useful intermediates leading to the 4"-amino compounds and processes for the preparation of the 4"-deoxy-4"-oxo-erythromycin A intermediates.

2. Description of the Prior Art

Erythromycin is an antibiotic formed during the culturing of a strain of Streptomyces erythreus in a suitable medium as taught in U.S. Pat. No. 2,653,899. Erythromycin, which is produced in two forms, A and B, is represented by the following structure:

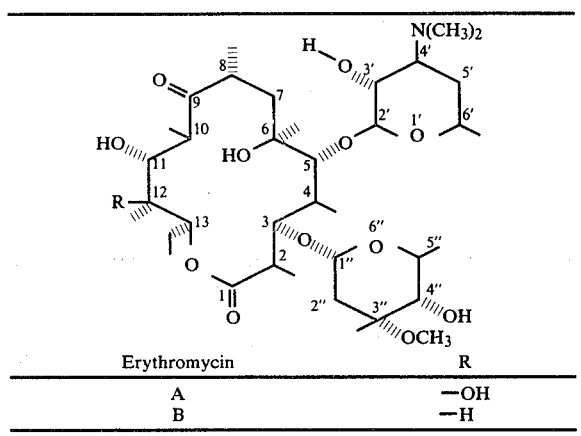

| Erythromycin | R |
|---|---|
| A | —OH |
| B | —H |

The structure reveals that the antibiotic is comprised of three main portions: a sugar fragment known as cladinose, a second sugar moiety containing a basic amino substituent known as desosamine and a fourteen membered lactone ring referred to as erythronolide A or B or, as herein described, the macrolide ring. While the numbering system of the macrolide ring is in unprimed numbers, that of the desosamine is in primed numbers and that of cladinose in double-primed numbers.

Numerous derivatives of erythromycin have been prepared in an effort to modify its biological or pharmacodynamic properties.

U.S. Pat. No. 3,417,077 describes the reaction product of erythromycin and ethylene carbonate as a very active antibacterial agent. U.S. Pat. No. 3,884,903 discloses 4"-deoxy-4"-oxo-erythromycin A and B derivatives as being useful as antibiotics.

Erythromycylamine, the 9-amino derivative of erythromycin A, has been the subject of considerable investigation [British Pat. No. 1,100,504, Tetrahedron Letters, 1645 (1967) and Croatica Chemica Acta, 39, 273 (1967)] and some controversy as to its structural identity [Tetrahedron Letters, 157 (1970) and British Pat. No. 1,341,022]. Sulfonamide derivatives of erythromycylamine are reported in U.S. Pat. No. 3,983,103 to be useful as antibacterial agents. Other derivatives are also reported [Ryden, et al., J. Med. Chem., 16, 1059 (1973) and Massey, et al., J. Med. Chem., 17, 105 (1974)] to have in vitro and in vivo antibacterial activity.

SUMMARY OF THE INVENTION

It has now been discovered that certain novel 4"-deoxy-4"-amino-erythromycin A derivatives are outstanding as antibacterial agents. These compounds are represented by the formulae:

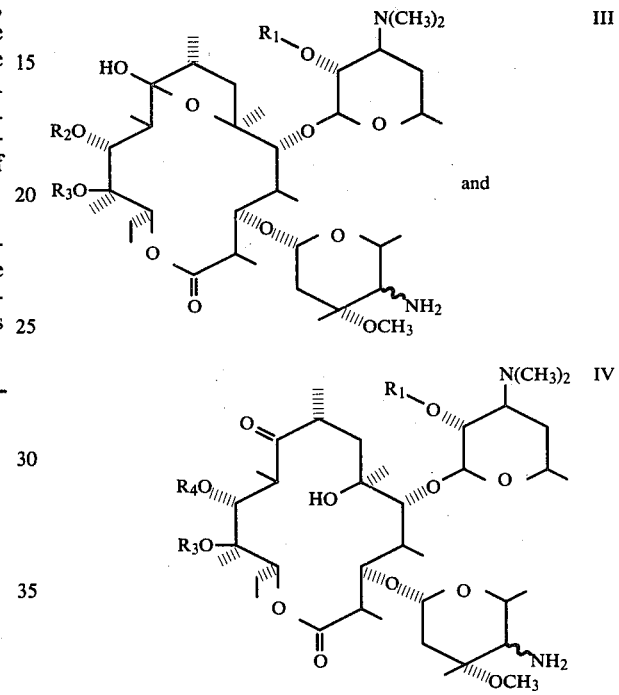

and a pharmaceutically acceptable acid addition salt thereof, wherein $R_1$ and $R_4$ are each hydrogen or alkanoyl of two to three carbon atoms; $R_2$ is alkanoyl of two to three carbon atoms; $R_3$ is hydrogen; $R_2$ and $R_3$ when taken together are

and $R_3$ and $R_4$ when taken together are

A preferred group of compounds within this class of chemotherapeutic agents are those of Formula III. Especially preferred within this group are those compounds wherein $R_2$ and $R_3$ when taken together are

A second preferred group of compounds in this class of antibacterial agents are those of Formula IV. Especially preferred within this group are those compounds wherein $R_4$ is hydrogen and also wherein $R_3$ and $R_4$ when taken together are

A second class of compounds of the present invention, useful as intermediates leading to the antibacterial agents of Formulae III and IV, are represented as follows:

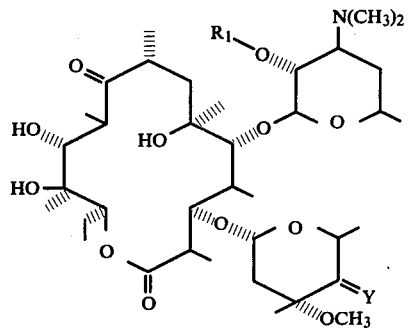

I and

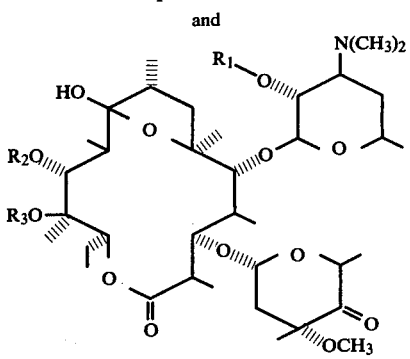

II wherein $R_1$ is hydrogen or alkanoyl of two to three carbon atoms; $R_2$ is alkanoyl of two to three carbon atoms; Y is N—OH or

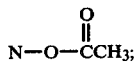

$R_3$ is hydrogen; and $R_2$ and $R_3$ when taken together are

Preferred within this class of intermediates are those compounds of Formula I. Especially preferred within this group of intermediates are those compounds wherein $R_1$ is hydrogen or acetyl.

A second group of preferred intermediates are those of Formula II. Especially preferred within this group are those intermediates wherein $R_1$ is hydrogen and also those wherein $R_1$ is acetyl.

Also within the scope of the present invention are processes for preparing intermediate compounds of the formulae:

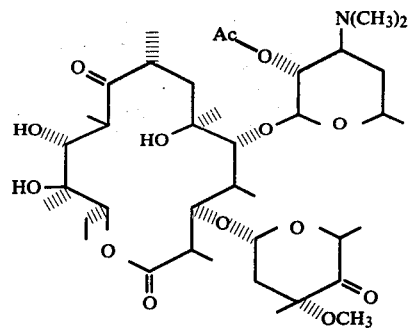

I and

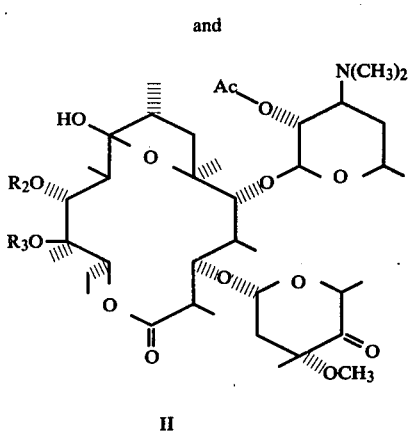

II wherein Ac and $R_2$ are each alkanoyl of two to three carbon atoms; $R_3$ is hydrogen; and $R_2$ and $R_3$ when taken together are

which comprises reacting a compound selected from the group consisting of the formulae:

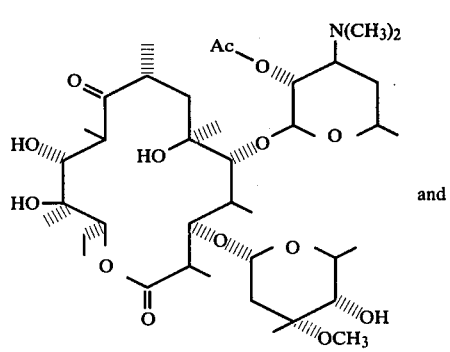

I' and

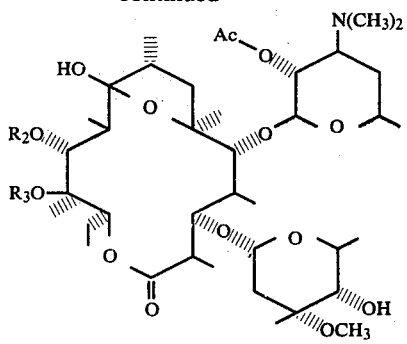

II′

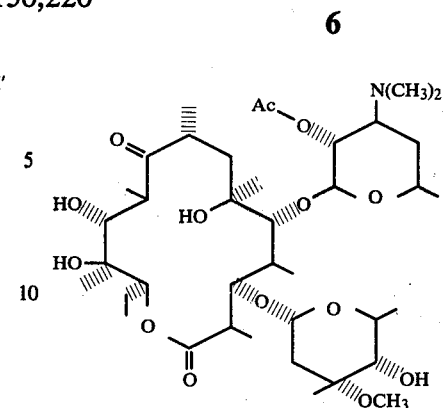

I′ and

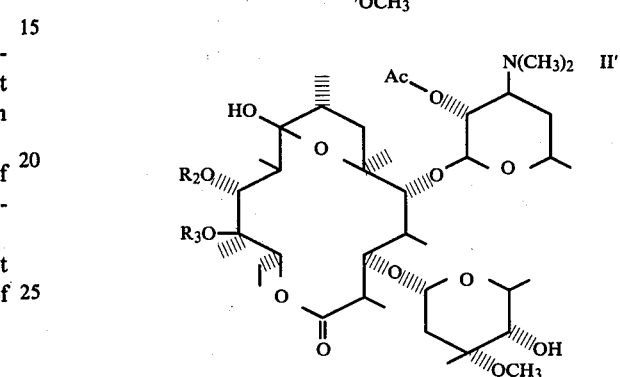

II′ with one mole each of dimethylsulfoxide and trifluoroacetic anhydride in a reaction-inert-solvent at about −30° to −65° C. followed by contacting the reaction mixture with at least one mole of triethylamine.

A preferred feature of this process is the oxidation of the compounds of Formula I′ and II′ wherein the reaction-inert-solvent is methylene chloride.

A second process within the scope of the present invention comprises the preparation of compounds of the formulae:

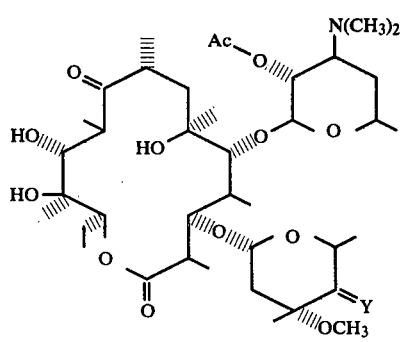

I and

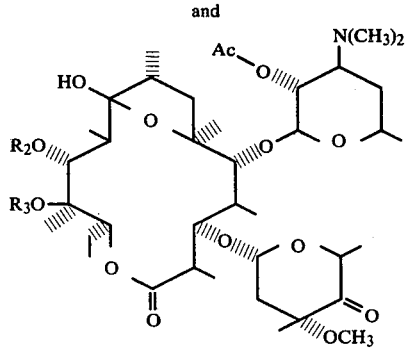

II wherein Ac and $R_2$ are each alkanoyl of two to three carbon atoms; $R_3$ is hydrogen; and $R_2$ and $R_3$ when taken together are

which comprises reacting a compound selected from the group consisting of the formulae:

with one mole each of N-chlorosuccinimide and dimethylsulfide and in a reaction-inert-solvent at about 0° to −25° C. followed by contacting the reaction mixture with at least one mole of triethylamine.

A preferred feature of the claimed process is the use of toluene and benzene as the reaction-inert solvent.

Throughout the present invention, the stereochemical designation of the substituents on the sugars and macrolide ring, with the exception of epimerication at the 4″-position where noted, are those of the naturally occurring erythromycin A.

Also considered within the purview of the present invention are erythromycin B derivatives which correspond to those of Formulae I and II. These erythromycin B compounds are useful intermediates and are prepared by the same synthetic procedure as herein described for the erythromycin A compounds. The erythromycin B intermediates are also converted, by the herein described procedures, to erythromycin B amines corresponding to the compounds of Formulae III and IV of the present invention. The erythromycin B amines are also useful as antibacterial agents.

DETAILED DESCRIPTION OF THE INVENTION

In accordance with the processes employed for synthesizing the 4″-deoxy-4″-amino-erythromycin A derived antibacterial agents of the present invention, the following scheme, starting with a 2′-alkanoyl-erythromycin A, or derivative thereof, are represented as follows:

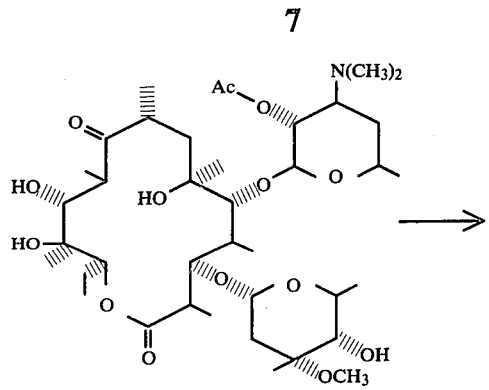

I'

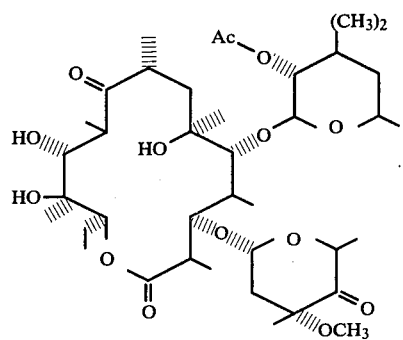

I (Y=O)

and

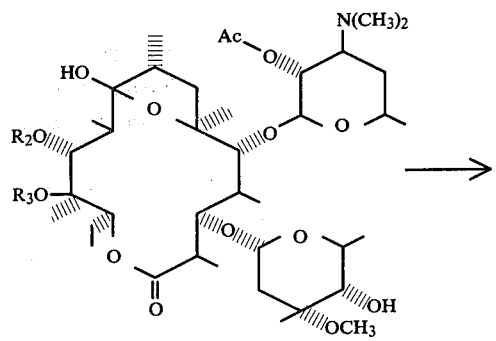

II'

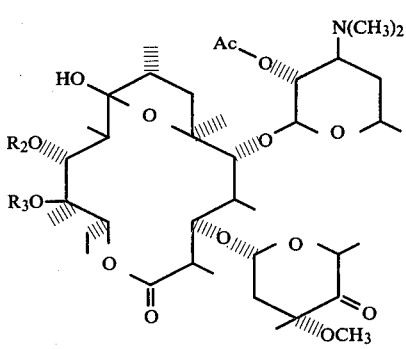

II

The selective oxidation of I' and II' to I and II, respectively, (Y=O) is the first of the processes of the present invention and comprises reacting the compounds I' and II' with trifluoroacetic anhydride and dimethylsulfoxide followed by the addition of a tertiary amine such as triethylamine.

In practice, the trifluoroacetic anhydride and dimethylsulfoxide are initially combined in a reaction-inert-solvent at about −65° C. After ten to fifteen minutes the alcohols I' and II' are added at such a rate that the temperature is maintained at about −65° C. and does not rise above −30° C. At temperatures above −30° C. the trifluoroacetic anhydride - dimethylsulfoxide complex is not stable. The reaction temperature is maintained below −30° and −65° C. for about fifteen minutes and is then lowered to about −70° C. A tertiary amine is added all at once and the reaction allowed to warm during a ten to fifteen minute period. The reaction mixture is subsequently treated with water and worked up.

Regarding the quantities of reactants, for each mole of alcohol substrate employed, one mole each of the trifluoroacetic anhydride and dimethylsulfoxide are required. Experimentally, it is advantageous to employ a 1–5 fold excess of the anhydride and dimethylsulfoxide in order to hasten the completion of the reaction. The tertiary amine employed should correspond to the molar amount of trifluoroacetic anhydride used.

The reaction-inert-solvent utilized in this process should be one which appreciably solubilizes the reactants and does not react to any great extent with either the reactants or the products formed. Since this oxidation process is conducted at −30° to −65° C., it is preferred that, in addition to having the above characteristics, said solvent possess a freezing point below the reaction temperature. Such solvents or mixtures thereof which meet these criteria are toluene, methylene chloride, ethyl acetate, chloroform or tetrahydrofuran. Solvents which meet the above requirements but which have a freezing point above the reaction temperature can be employed in minor amounts in combination with one of the preferred solvents. The especially preferred solvent for this process is methylene chloride.

The preferred compounds prepared by this process are 2'-acetyl-4''-deoxy-4''-oxo-erythromycin A, 11,2'-diacetyl-4''-deoxy-4''-oxo-erythromycin A, 6,9-hemiketal and 2'-acetyl-4''-deoxy-4''-oxo-erythromycin A 6,9-hemiketal 11,12-carbonate ester.

The reaction time is not critical and is dependent on reaction temperature and the inherent reactivity of the starting reagents. At temperatures of about −30° to −65° C., the reaction is complete in fifteen to thirty minutes.

As to the order of addition of the reagents, it is preferred that the trifluoroacetic anhydride be combined with the dimethylsulfoxide followed by the addition of the requisite alcohol substrate. It is further suggested, as hereinbefore mentioned, that the temperature of the reaction is kept below −30° C. This is in accordance with the teaching of Omura, et al., *J. Org. Chem.*, 41, 957 (1976).

The second process of the claimed invention, used to prepare intermediates leading to the useful antibacterial agents, is represented by the following scheme:

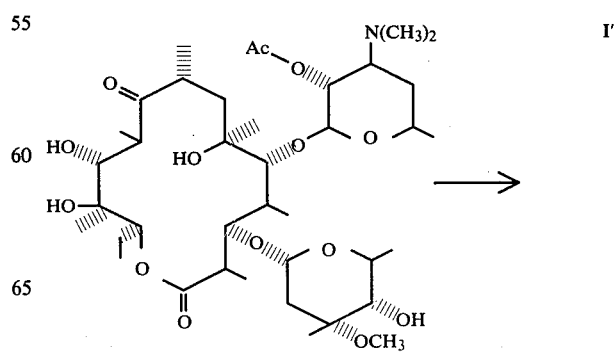

I'

-continued

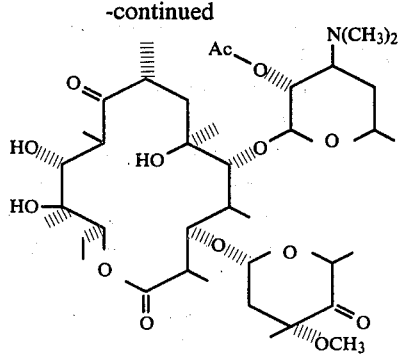

and

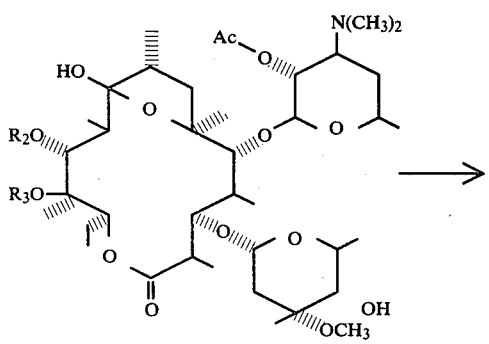

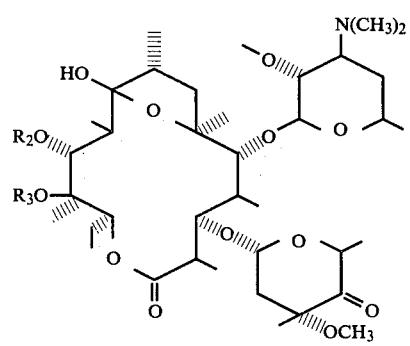

The second process represents an oxidation reaction wherein the 4″-hydroxy substituent of I′ and II′, wherein Ac and $R_2$ are each alkanoyl of two to three carbon atoms, $R_3$ is hydrogen, $R_2$ and $R_3$ when taken together are

is oxidized to a 4″-deoxy-4″-oxo-erythromycin A compound.

The process comprises the use of N-chlorosuccinimide and dimethylsulfide as the oxidizing agent. In practice, these two reagents are first combined together in a reaction-inert-solvent at about 0° C. After ten to twenty minutes the temperature is lowered to 0° to −25° C. and the alcohol substrate I′ or II′ is added, while maintaining the aforementioned temperature. After two to four hours reaction time, a tertiary amine, such as triethylamine, is added the reaction mixture hydrolyzed and worked up.

Regarding the quantities of reactants, for each mole of alcohol substrate employed, one mole each of the N-chlorosuccinimide and dimethylsulfide are required. Experimentally, it is advantageous to employ a 1-20 fold excess of the succinimide and sulfide reactants in order to hasten the completion of the reaction. The tertiary amine employed should correspond to the molar amount of succinimide used.

The reaction-inert-solvent utilized in the claimed process should be one which appreciably solubilizes the reactants and does not react to any appreciable extent with either the reactants or the products formed. Since the reaction is conducted at about 0° to −25° C., it is preferred that, in addition to having the above characteristics, it should possess a freezing point below the reaction temperature. Such solvents or mixtures thereof which meet these criteria are toluene, ethyl acetate, chloroform, methylene chloride or tetrahydrofuran. Solvents which meet the above requirements but which have a freezing point above the reaction temperature can also be employed in minor amounts in combination with one or more of the preferred solvents. The especially preferred solvent for the claimed process is toluene-benzene.

The preferred compounds prepared by this process are 11,2′-diacetyl-4″-deoxy-4″-oxo-erythromycin A 6,9-hemiketal, 2′-acetyl-4″-deoxy-4″-oxo-erythromycin A 6,9-hemiketal 11,12-carbonate ester and 2′-acetyl-4″-deoxy-4″-oxo-erythromycin A.

Reaction time is not critical and is dependent on concentration, reaction temperature and the inherent reactivity of the reagents. At a reaction temperature of 0° to −25° C. the reaction time is about two to four hours.

Regarding the order of addition, as previously mentioned, it is preferred that the alcohol substrate I′ or II′ be added to the premixed succinimide derivative and dimethylsulfide.

Both the herein described processes are viewed as unique because of the selectivity of the oxidation which takes place exclusively at the 4″-hydroxy substituent, leaving other secondary alcohols in the molecule unaffected.

The useful intermediate 4″-deoxy-4″-oxo compounds of the formula:

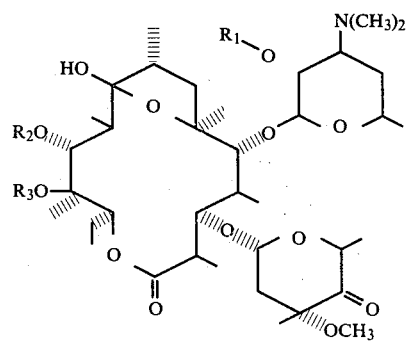

wherein $R_1$ and $R_2$ are each alkanoyl of two to three carbon atoms and $R_3$ is hydrogen are prepared by treating a compound of the formula:

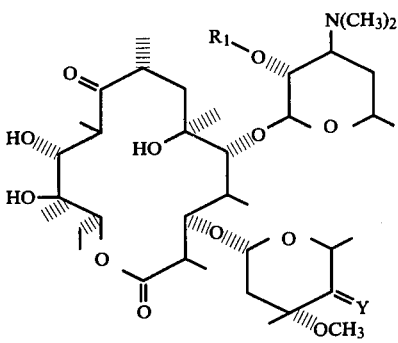

wherein Y is O, $R_1$ is alkanoyl of two to three carbon atoms, with an alkanoic anhydride ($R_2O$) and pyridine.

In practice, the ketone I is contacted with an excess of the anhydride in pyridine as the solvent. It is preferred that as much as a four fold excess of the anhydride be employed in the reaction.

The reaction is conveniently carried out at ambient temperatures. At these reaction temperatures the reaction time is about twelve to twenty-four hours.

Removal of the alkanoyl moiety at the 2'-position of the intermediate ketones I (Y=O) and II is carried out through a solvolysis reaction wherein the 2'-alkanoyl-4"-deoxy-4"-oxo-erythromycin A related compound is allowed to stir with an excess of methanol overnight at room temperature. Removal of the methanol and subsequent purification, where necessary, of the residual product provides for compounds of Formulae I (Y=O) and II wherein $R_1$ is hydrogen.

As previously mentioned, the ketones of Formulae I (Y=O) and II are useful intermediates leading to the 4"-deoxy-4"-amino-erythromycin A antibacterial agents of the present invention of formulae III and IV. Preferred as intermediates in this group are 2'-acetyl-4"-deoxy-4"-oxo-erythromycin A 6,9-hemiketal 11,12-carbonate ester and 4"-deoxy-4"-oxo-erythromycin A 6,9-hemiketal 11,12-carbonate ester.

Several synthetic pathways can be employed in the preparation of the antibacterial agents of Formulae III and IV from the requisite ketones I (Y=O) and II.

Preparation of the 4"-deoxy-4"-amino-erythromycin A compounds of Formula III is carried out by the condensation of the ketones II with the ammonium salt of a lower alkanoic acid and the subsequent reduction of the in situ generated imine. The term "lower alkanoic" refers, in this instance, to an acid having two to four carbon atoms.

In practice, a solution of the ketone II in a lower alkanol, such as methanol or isopropanol, is treated with the ammonium salt of a lower alkanoic acid, such as acetic acid, and the cooled reaction mixture treated with the reducing agent sodium cyanoborohydride. The reaction is allowed to proceed at room temperature for several hours before it is subsequently hydrolyzed and the product isolated.

Although one mole of the ammonium alkanoate is needed per mole of ketone, it is preferred that an excess, as great as ten fold, be employed in order to ensure complete and rapid formation of the imine. Such excess amounts appear to have little deleterious effects on the quality of the product.

Regarding the amount of reducing agent to be employed per mole of ketone, it is preferred that about two moles of sodium cyanoborohydride per mole of ketone be used.

The reaction time will vary with concentration, reaction temperature and the inherent reactivity of the reagents. At room temperature, the preferred reaction temperature, the reaction is substantially complete after two to three hours.

When the lower alkanol solvent is methanol there is, as previously mentioned, substantial solvolysis of any alkanoyl group at the 2'-position. In order to avoid removal of such a moiety it is preferred that isopropanol be used as the reaction solvent.

The preferred ammonium alkanoate, as previously indicated, for this reaction is ammonium acetate.

In isolating the desired 4"-deoxy-4"-amino-erythromycin A derivatives from any non-basic by-products or starting material, advantage is taken of the basic nature of the final product. Accordingly, an aqueous solution of the product is extracted over a range of gradually increasing pH such that neutral or non-basic materials are extracted at lower pH's and the product at a pH of greater than 5. The extracting solvents, either ethyl acetate or diethyl ether, are backwashed with brine and water, dried over sodium sulfate and the product obtained by removal of the solvent. Additional purification, if necessary, can be effected by column chromatography on silica gel according to known procedures.

As previously mentioned, solvolysis of the 2'-alkanoyl group from the appropriate 2'-alkanoyl-4"-deoxy-4"-amino-erythromycin A derivative can be effected by allowing a methanol solution of said compound to stand overnight at ambient temperatures.

During the reductive amination of ketones of Formula II wherein $R_2$ and $R_3$ when taken together are

and $R_1$ is alkanoyl of two to three carbon atoms or hydrogen, it is noted that amines related to both Formulae III and IV are produced. This is represented by the following scheme:

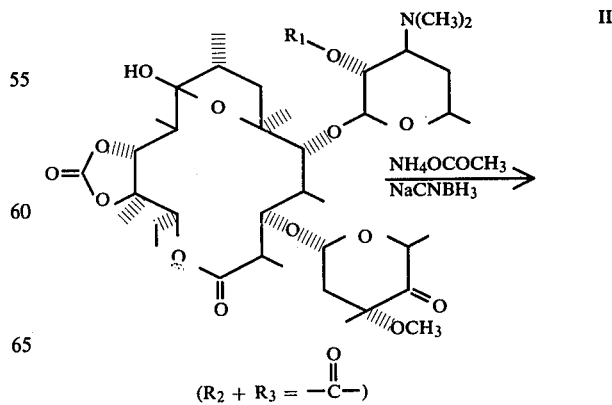

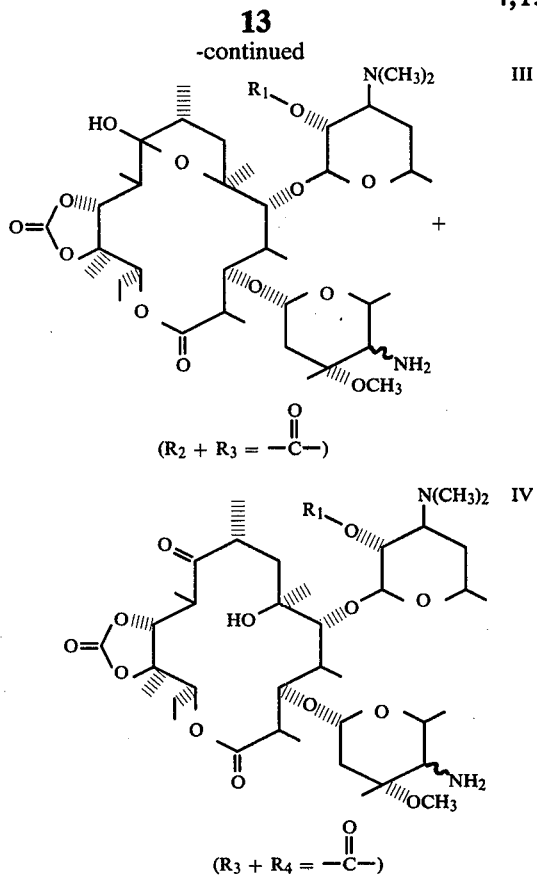

(R₂ + R₃ = —C(=O)—) III (R₃ + R₄ = —C(=O)—) IV

The amine products III and IV as represented are conveniently separated by selective crystallization from diethyl ether. Recrystallization of the mixture of III and IV as represented from acetone-water induces hemiketal formation in the amine of Formula IV resulting in the isolation of III as the sole product.

The first direct synthetic pathway to the amine compounds of Formula IV is the same route as discussed previously and comprises the condensation of the ketone I with an ammonium alkanoate followed by reduction of the in situ generated imine with sodium cyanoborohydride.

Compounds of Formula IV, wherein $R_1$, $R_3$ and $R_4$ are as previously defined, are also prepared by the reduction of the aforementioned imine using hydrogen and an appropriate hydrogenation catalyst. Experimentally, the appropriate ketone (I) in a lower alkanol, such as methanol or isopropanol, is treated with the ammonium salt of a lower alkanoic acid, such as acetic acid, and the hydrogenation catalyst, and the mixture shaken in a hydrogen atmosphere until the reaction is essentially complete.

Although one mole of the ammonium alkanoate is needed per mole of ketone, it is preferred that an excess, as great as ten fold, be employed in order to insure complete and rapid formation of the imine. Such excess amounts appear to have little deleterious effects on the quality of the product.

The hydrogenation catalyst can be selected from a wide range of agents; Raney nickel and 5–10 percent palladium-on-charcoal are, however, the preferred catalysts. These may be used in varying amounts depending on how fast the reaction is to be completed. Amounts from 10–200 percent of the weight of I can be employed effectively.

The pressure of the hydrogen gas in the hydrogenation vessel also influences the rate of reaction. It is preferred, for the convenience of reaction time, that an initial pressure of 50 p.s.i, be employed. It is also preferred, for convenience, that the reduction be carried out at ambient temperatures.

Reaction time is dependent on a number of factors including temperature, pressure, concentration of the reactants and the inherent reactivity of the reagents. Under the aforementioned preferred conditions the reaction is complete in 12 to 24 hours.

The product is isolated by filtration of the spent catalyst and removal of the solvent in vacuo. The residual material is subsequently treated with water and the product isolated from non-basic materials by extraction of the basic product from water at varying pH's previously described.

As previously indicated, when the lower alkanol solvent is methanol there is substantial solvolysis of any alkanoyl group at the 2'-position. In order to avoid removal of such a moiety it is preferred that isopropanol be used as the reaction solvent.

The second synthetic route to the 4''-deoxy-4''-amino-erythromycin A antibacterial agents of Formula IV comprises initial conversion of the ketones of Formula I (Y=O) to an oxime or oxime derivative, i.e., Y=N—OH and

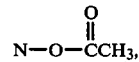

$$N-O-\overset{O}{\underset{\|}{C}}CH_3,$$

followed by reduction of the oxime or derivative thereof.

The oximes of the ketones I (Y=O) are prepared by reacting said ketones with hydroxylamine hydrochloride and barium carbonate in methanol or isopropanol at room temperature. In practice, it is preferred that an excess of hydroxylamine be employed, and as much as a three fold excess provides the desired intermediate in good yields. Employing ambient temperatures and an excess of the hydroxylamine allows for the preparation of the desired oxime derivative in a reaction period of one to three hours. The barium carbonate is used in molar quantities twice that of the hydroxylamine hydrochloride employed. The product is isolated by addition of the reaction mixture to water followed by basification to pH 9.5 and extraction with a water-immiscible solvent such as ethyl acetate.

Alternately, the reaction mixture can be filtered and the filtrate concentrated in vacuo to dryness. The residue is subsequently partitioned between water at pH 9.0–9.5 and a water-immiscible solvent.

Preparation of the O-acetyloxime compounds of Formula I

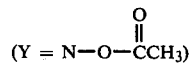

$$(Y = N-O-\overset{O}{\underset{\|}{C}}CH_3)$$

is effected by acetylation of the corresponding oxime. Experimentally, one mole of the oxime is reacted with one mole of acetic anhydride in the presence of one mole of pyridine or triethylamine. The use of an excess of the anhydride and pyridine aid in the completion of the reaction and an excess of 30–40% is preferred. The reaction is best conducted in an aprotic solvent such as benzene or ethyl acetate at room temperature overnight. On completion of the reaction, water is added, the pH adjusted to 9.0 and the product separated in the solvent layer.

The preferred oxime and oxime derivatives which are useful intermediates leading to the 4''-deoxy-4''-amino-erythromycin A derived antibacterial agents include 2'-acetyl-4''-deoxy-4''-oxo-erythromycin A oxime, 2'-acetyl-4''-deoxy-4''-oxo-erythromycin A O-acetyloxime, 4''-deoxy-4''-oxo-erythromycin A oxime and 4''-deoxy-4''-oxo-erythromycin A O-acetyloxime.

Reduction of the ketone derivatives (Y=N—OH or

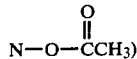

is carried out by catalytic hydrogenation wherein a solution of the oxime or derivative thereof in a lower alkanol, such as isopropanol, and a Raney nickel catalyst is shaken in a hydrogen atmosphere at an intial pressure of 1000 p.s.i. at room temperature overnight. Filtration of the spent catalyst followed by removal of the solvent from the filtrate provides for the isolation of the desired 4''-deoxy-4''-amino antibacterial agent related to Formula IV. If methanol is employed as the solvent in this reduction, solvolysis of a 2'-alkanoyl moiety is probable. In order to avoid this side-reaction, isopropanol is employed.

Preferred among these 4''-deoxy-4''-amino-erythromycin A derived antibacterial agents of Formulae III and IV are both epimers of 4''-deoxy-4''-amino-erythromycin A 6,9-hemiketal 11,12-carbonate ester and of 4''-deoxy-4''-amino-erythromycin A, of 4''-amino-erythromycin A 11,12-carbonate ester.

In the utilization of the chemotherapeutic activity of those compounds of Formulae III and IV of the present invention which form salts, it is preferred, of course, to use pharmaceutically acceptable salts. Although water-insolubility, high toxicity, or lack of crystalline nature may make some particular salt species unsuitable or less desirable for use as such in a given pharmaceutical application, the water insoluble or toxic salts can be converted to the corresponding pharmaceutically bases by decomposition of the salt as described above, or alternately they can be converted to any desired pharmaceutically acceptable acid addition salt.

Examples of acids which provide pharmaceutically acceptable anions are hydrochloric, hydrobromic, hydroiodic, nitric, sulfuric, or sulfurous, phosphoric, acetic, lactic, citric, tartaric, succinic, maleic, gluconic and aspartic acids.

As previously mentioned, the stereochemistry of the starting materials leading to the antibacterial agents of the present invention is that of the natural material. The oxidation of the 4''-hydroxyl group to a ketone and the subsequent conversion of said ketone to the 4''-amines presents an opportunity for the stereochemistry of the 4''-substituent to change from that of the natural product. Accordingly, when the compounds I (Y=O) and II are converted to amines by one of the hereinbefore described procedures, it is possible that two epimeric amines are formed. Experimentally, it is observed that both epimeric amines are present in the final product in varying ratios depending on the choice of synthetic method. If the isolated product consists predominantly of one of the epimers, said epimer can be purified by repeated recrystallization from a suitable solvent to a constant melting point. The other epimer, the one present in smaller amounts in the originally isolated solid material, is the predominant product in the mother liquor. It can be recovered therefrom by methods known to those skilled in the art, as for example, the evaporation of the mother liquor and repeated recrystallization of the residue to a product of constant melting point.

Although said mixture of epimers can be separated by methods known to those skilled in the art, for practical reasons it is advantageous to use said mixture as it is isolated from the reaction. However, it is frequently advantageous to purify the mixture of epimers by at least one recrystallization from an appropriate solvent, subjecting it to column or high pressure liquid chromatography, solvent partitioning or by trituration in an appropriate solvent. Said purification, while not necessarily separating the epimers, removes such extraneous materials as starting materials and undesirable by-products.

The absolute stereochemical assignment for the epimers has not been completed. Both epimers of a given compound, however, exhibit the same type of activity, e.g., as antibacterial agents.

The novel 4''-deoxy-4''-amino-erythromycin A derivatives described herein exhibit in vitro activity against a variety of Gram-positive microorganisms, e.g., *Staphylococcus aureus* and *Streptococcus pyogenes,* and against certain Gram-negative microorganisms such as those of spherical or ellisoidal shape (cocci). Their activity is readily demonstrated by in vitro tests against various microorganisms in a brain-heart infusion medium by the usual two-fold serial dilution technique. Their in vitro activity renders them useful for topical application in the form of ointments, creams and the like; for sterilization purposes, e.g., sick-room utensils; and as industrial antimicrobials, for example, in water treatment, slime control, paint and wood preservation.

For in vitro use, e.g., for topical application, it will often be convenient to compound the selected product with a pharmaceutically-acceptable carrier such as vegetable or mineral oil or an emollient cream. Similarly, they may be dissolved or dispersed in liquid carriers or solvents, such as water, alcohol, glycols or mixtures thereof or other pharmaceutically-acceptable inert media; that is, media which have no harmful effect on the active ingredient. For such purposes, it will generally be acceptable to employ concentrations of active ingredients of from about 0.01 percent to about 10 percent by weight based on total composition.

Additionally, many compounds of this invention and their acid addition salts are active versus Gram-positive and certain Gram-negative microorganisms, e.g., *Pasteurella multocide* and *Neisseria sicca,* in vivo via the oral and/or parenteral routes of administration in animals, including man. Their in vivo activity is more limited as regards susceptible organisms and is determined by the usual procedure which comprises infecting mice of substantially uniform weight with the test organism and subsequently treating them orally or subcutaneously with the test compound. In practice, the mice, e.g., 10, are given an intraperitoneal inoculation of suitable diluted cultures containing approximately 1 to 10 times the $LD_{100}$ (the lowest concentration of organisms required to product 100% deaths). Control tests are simultaneously run in which mice receive inoculum of lower dilutions as a check on possible variation in virulence of the test organism. The test compound is administered 0.5 hour post-inoculation, and is repeated 4, 24 and 48 hours later. Surviving mice are held for four days after the last treatment and the number of survivors is noted.

When used in vivo, these novel compounds can be administered orally or parenterally, e.g., by subcutaneous or intramuscular injection, at a dosage of from about 1 mg./kg. to about 200 mg./kg. of body weight per day. The favored dosage range is from about 5 mg./kg. to about 100 mg./kg. of body weight per day and the preferred range from about 5 mg./kg. to about 50 mg./kg. of body weight per day. Vehicles suitable for parenteral injection may be either aqueous such as water, isotonic saline, isotonic dextrose, Ringer's solution, or non-aqueous such as fatty oils of vegetable origin (cotton seed, peanut oil, corn, sesame), dimethylsulfoxide and other non-aqueous vehicles which will not interfere with therapeutic efficiency of the preparation and are non-toxic in the volume or proportion used (glycerol, propylene glycol, sorbitol). Additionally, compositions suitable for extemporaneous preparation of solutions prior to administration may advantageously be made. Such compositions may include liquid diluents, for example, propylene glycol, diethyl carbonate, glycerol, sorbitol, etc.; buffering agents, hyaluronidase, local anesthetics and inorganic salts to afford desirable pharmacological properties. These compounds may also be combined with various pharmaceutically-acceptable inert carriers including solid diluents, aqueous vehicles, non-toxic organic solvents in the form of capsules, tablets, lozenges, troches, dry mixes, suspensions, solutions, elixirs and parenteral solutions or suspensions. In general, the compounds are used in various dosage forms at concentration levels ranging from about 0.5 percent to about 90 percent by weight of the total composition.

The following examples are provided solely for the purpose of illustration and not to be construed as limitations of this invention, many variations of which are possible without departing from the spirit or scope thereof.

EXAMPLE 1

2'-Acetyl-4''-deoxy-4''-oxo-erythromycin A

To 3 ml. of methylene chloride and 0.328 ml. of dimethylsulfoxide cooled to about −65° C. and maintained under a nitrogen atmosphere is added 0.652 ml. of trifluoroacetic anhydride. After about a minute a white slurry forms indicating the presence of the trifluoroacetic anhydride-dimethylsulfoxide complex. To the resulting slurry is added dropwise a solution of 1.0 g. of 2'-acetylerythromycin A.ethyl acetate, obtained by recrystallization of 2'-acetylerythromycin A from ethyl acetate, in 7 ml. of methylene chloride keeping the temperature at about −65° C. The resulting mixture is allowed to stir for 15 min. at about −60° C. and is then cooled to −70° C. Triethylamine (1.61 ml.) is added rapidly to the reaction mixture and the cooling bath is removed. After stirring for 15 min. the solution is added to 10 ml. of water and the pH of the aqueous phase adjusted to 10. The organic phase is separated, washed successively with water (3×10 ml.) and brine solution (1×10) and dried over sodium sulfate. Removal of the solvent under reduced pressure gives 929 mg. of the crude product. Recrystallization from methylene chloride-hexane gives 320 mg. of the purified product, m.p. 105°–108° C.

NMR (δ, CDCl$_3$): 3.28 (3H)s, 2.21 (6H)s and 2.03 (3H)s.

In a similar manner, starting with 2'-propionylerythromycin A.ethyl acetate and following the above procedure gives 2'-propionyl-4''-deoxy-4''-oxo-erythromycin A.

EXAMPLE 2

4''-Deoxy-4''-oxo-erythromycin A

A solution of 4.0 g. of 2'-acetyl-4''-deoxy-4''-oxo-erythromycin A in 75 ml. of methanol is allowed to stir at ambient temperatures for 20 hrs. The solvent is removed in vacuo and the residual white foam recrystallized from methylene chloride-hexane, 3.44 g., m.p. 170.5°–172.5° C.

NMR (δ, CDCl$_3$): 3.36 (3H)s and 2.33 (6H)s.

A product identical with the above is isolated when 2'-propionyl-4''-deoxy-4''-oxo-erythromycin A is treated with methanol at room temperature.

EXAMPLE 3

2'-Acetyl-4''-deoxy-4''-oxo-erythromycin A

To a stirring solution of 13.7 g. of 4''-deoxy-4''-oxo-erythromycin A in 100 ml. of ethyl acetate is added 2.3 ml. of acetic anhydride and the resulting reaction mixture allowed to stir at room temperature for 2 hrs. The solution is added to 100 ml. of water and the pH of the aqueous phase raised to 9.5 by the addition of 6 N sodium hydroxide solution. The organic layer is separated, dried over sodium sulfate and concentrated to give 14.5 g. of a white foam identical, after recrystallization from methylene chloride-hexane, with the product of Example 1.

EXAMPLE 4

2'-Acetyl-4''-deoxy-4''-oxo-erythromycin A oxime

To 500 ml. of methanol is added 10.8 g. of 2'-acetyl-4''-deoxy-4''-oxo-erythromycin A, 1.94 g. of hydroxylamine hydrochloride and 11.0 g. of barium carbonate, and the resulting suspension allowed to stir at room temperature for 3.5 hrs. The mixture is filtered and the filtrate concentrated under reduced pressure. The residual foam is taken up in ethyl acetate which is subsequently washed with water at pH 9.5. The organic phase is separated, dried over sodium sulfate and concentrated in vacuo to give 10.6 g. of the desired product.

NMR (δ, CDCl$_3$): 3.33 (3H)s, 2.30 (6H)s and 2.06 (3H)s.

EXAMPLE 5

2'-Acetyl-4''-deoxy-4''-oxo-erythromycin A O-acetyloxime

To a solution of 330 mg. of 2'-acetyl-4''-deoxy-4''-oxo-erythromycin A oxime in 30 ml. of ethyl acetate is added with stirring 64.2 μl of acetic anhydride, and the reaction allowed to stir overnight at room temperature. An additional 15.8 μl of acetic anhydride and 23.4 μl of triethylamine are added and the stirring continued for 4 hrs. The reaction mixture is added to water and the pH adjusted to about 9.0. The ethyl acetate layer is separated, dried over sodium sulfate and concentrated under vacuum to give 300 mg. of the desired product.

NMR (δ, CDCl$_3$): 3.38 (3H)s, 2.25 (6H)s, 2.20 (3H)s, 2.05 (3H)s and 1.56 (3H)s.

In a similar manner by substituting 2'-propionyl-4''-deoxy-4''-oxo-erythromycin A oxime and 4''-deoxy-4''-oxo-erythromycin A oxime for 2'-acetyl-4''-deoxy-4''-oxo-erythromycin A oxime in the above procedure, the respective O-acetyl derivatives are prepared.

EXAMPLE 6

2'-Acetyl-4''-deoxy-4''-amino-erythromycin A

A mixture of 14.0 g. of 2'-acetyl-4''-deoxy-4''-oxo-erythromycin A O-acetyloxime and 60 g. of isopropanol washed Raney nickel in 400 ml. of isopropanol is agitated in a hydrogen atmosphere at an initial pressure of 1000 p.s.i. overnight at room temperature. The catalyst is filtered and the filtrate concentrated to a white foam. The residue is redissolved in 400 ml. of isopropanol and combined with 50 g. of fresh isopropanol washed Raney nickel. The hydrogenation is continued overnight at room temperature and an initial hydrogen pressure of 1000 p.s.i. The catalyst is filtered and the filtrate concentrated in vacuo to dryness to give 8.1 g. of the desired product.

EXAMPLE 7

Starting with the appropriate O-acetyloxime and employing the procedure of Example 6, the following 4''-amino-erythromycin A analogs are prepared:

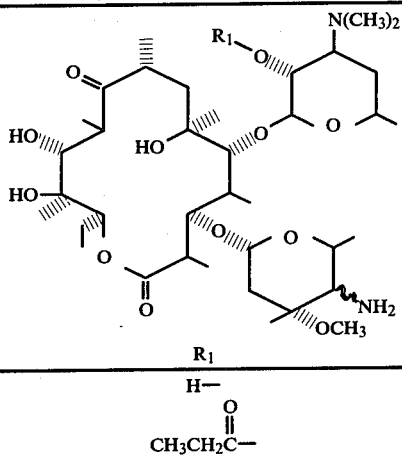

| $R_1$ |
|---|
| H— |
| $CH_3CH_2\overset{O}{\underset{\|}{C}}-$ |

EXAMPLE 8

4''-Deoxy-4''-amino-erythromycin A

A solution of 2.17 g. of 2'-acetyl-4''-deoxy-4''-amino-erythromycin A in 50 ml. of methanol is allowed to stir at room temperature overnight. The solvent is removed under reduced pressure and the residual foam treated with a mixture of 50 ml. of chloroform and 50 ml. of water. The pH of the aqueous layer is adjusted to 9.5 and the organic layer separated. The chloroform layer is treated with fresh water and the pH adjusted to 4.0. The pH of the acid aqueous layer containing the product is gradually adjusted to 5, 6, 7, 8 and 9 by the addition of base, being extracted at each pH with fresh chloroform. The extracts at pH 6 and 7 contain the major portion of the product and these are combined and treated with fresh water at pH 4. The aqueous layer is again adjusted through pH 5, 6 and 7, being extracted at each pH with fresh chloroform. The chloroform extract at pH 6 is dried over sodium sulfate and concentrated to give 249 mg. of the product as an epimeric mixture.

NMR (δ, CDCl₃): 3.30 (1H)s, 3.26 (2H)s, 2.30 (6H)s and 1.46 (3H)s.

In a similar manner, 4''-deoxy-4''-amino-erythromycin A is prepared by the methanol solvolysis of 2'-propionyl-4''-deoxy-4''-amino-erythromycin A.

EXAMPLE 9

4''-Deoxy-4''-amino-erythromycin A

To a stirring solution of 3.0 g. of 4''-deoxy-4''-oxo-erythromycin A in 30 ml. of methanol under a nitrogen atmosphere is added 3.16 g. of dry ammonium acetate. After 5 min. 188 mg. of sodium cyanoborohydride is washed into the reaction mixture with 5 ml. of methanol and the reaction allowed to stir at room temperature overnight. The light yellow solution is poured into 300 ml. of water and the pH adjusted to 6.0. The aqueous is extracted at pH6, 7, 7.5, 8, 9 and 10 using 125 ml. of diethyl ether for each extraction. The extracts at pH 8, 9 and 10 are combined and washed with 125 ml. of fresh water. The separated aqueous layer is extracted with ether (1×100 ml.) at pH 7, ethyl acetate (1×100 ml.) at pH 7, ether (1×100 ml.) at pH 7.5, ethyl acetate (1×100 ml.) at pH 7.5 and ethyl acetate (1×100 ml.) at pH 8, 9 and 10. The ethyl acetate extracts at pH 9 and 10 are combined, washed with a saturated brine solution and dried over sodium sulfate. Removal of the solvent in vacuo gives 30 mg. of an epimeric mixture of the desired product as an ivory colored foam.

EXAMPLE 10

4''-Deoxy-4''-amino-erythromycin A (single epimer)

A solution of 10.0 g. of the epimeric mixture of 2'-acetyl-4''-deoxy-4''-amino-erythromycin A in 150 ml. of methanol is allowed to stir at room temperature under nitrogen for 72 hrs. The solvent is removed in vacuo and the residue is dissolved in a stirring mixture of 150 ml. of water and 200 ml. of chloroform. The aqueous layer is discarded and 150 ml. of fresh water is added. The pH of the aqueous layer is adjusted to 5 and the chloroform layer is separated. The pH of the aqueous phase is subsequently adjusted to 5.5, 6, 7, 8 and 9, being extracted after each adjustment with 100 ml. of fresh chloroform. The chloroform extracts from pH 6, 7 and 8 are combined, successively with water and a saturated brine solution and dried over sodium sulfate. Removal of the solvent under reduced pressure gives 2.9 g. of an epimeric mixture of 4''-deoxy-4''-amino-erythromycin A. A 1.9 g. sample of the mixture is triturated with diethyl ether causing some of the undissolved foam to crystallize. The solids are filtered and dried to give 67 mg. of a single epimer of 4''-deoxy-4''-amino-erythromycin A, m.p. 140°–147° C.

EXAMPLE 11

11,2'-Diacetyl-4''-deoxy-4''-oxo-erythromycin A 6,9-hemiketal

A solution of 10 g. of 2'-acetyl-4''-deoxy-4''-oxo-erythromycin A in 250 ml. of pyridine is treated with 40 ml. of acetic anhydride and the resulting reaction mixture allowed to stand at room temperature for 10 days. The bulk of the solvent is removed in vacuo and the remaining concentrate added to a mixture of 150 ml. of water and 100 ml. of chloroform. The pH of the aqueous is raised to 9.0 and the chloroform separated, dried over sodium sulfate and concentrated to dryness.

NMR (δ, CDCl₃): 3.33 (3H)s, 2.26 (6H)s, 2.10 (3H)s, 2.03 (3H)s and 1.55 (3H)s.

EXAMPLE 12

Starting with the appropriate 4''-deoxy-4''-oxo-erythromycin A and requisite alkanoic anhydride and employing the procedure of Example 11, the following compounds are synthesized:

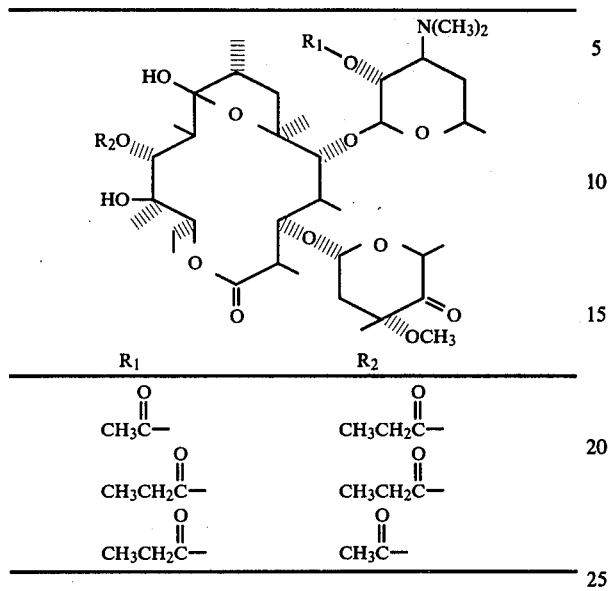

| R₁ | R₂ |
|---|---|
| $\underset{\text{CH}_3\text{C}-}{\overset{\text{O}}{\parallel}}$ | $\underset{\text{CH}_3\text{CH}_2\text{C}-}{\overset{\text{O}}{\parallel}}$ |
| $\underset{\text{CH}_3\text{CH}_2\text{C}-}{\overset{\text{O}}{\parallel}}$ | $\underset{\text{CH}_3\text{CH}_2\text{C}-}{\overset{\text{O}}{\parallel}}$ |
| $\underset{\text{CH}_3\text{CH}_2\text{C}-}{\overset{\text{O}}{\parallel}}$ | $\underset{\text{CH}_3\text{C}-}{\overset{\text{O}}{\parallel}}$ |

EXAMPLE 13

11-Acetyl-4''-deoxy-4''-oxo-erythromycin A 6,9-hemiketal

A solution of 3.0 g. of 11,2'-diacetyl-4''-deoxy-4''-oxo-erythromycin A 9,6-hemiketal in 50 ml. of methanol is allowed to stir under a nitrogen atmosphere overnight. The solvent is removed in vacuo to give the desired product (3.0 g.) as a yellow foam.

NMR (δ, CDCl₃): 3.35 (3H)s, 2.31 (6H)s, 2.13 (3H) and 1.55 (3H)s.

In a similar manner, the compounds of Example 12 are converted by the procedure of Example 13 to 11-acetyl-4''-deoxy-4''-oxo-erythromycin A 6,9-hemiketal and 11-propionyl-4''-deoxy-4''-oxo-erythromycin A 6,9-hemiketal.

EXAMPLE 14

11-Acetyl-4''-deoxy-4''-amino-erythromycin A 6,9-hemiketal

To a stirring solution of 4.4 g. of 11-acetyl-4''-deoxy-4''-oxo-erythromycin A 6,9-hemiketal and 4.38 g. of ammonium acetate in 75 ml. of methanol is added 305 mg. of 85% sodium cyanoborohydride. After stirring at room temperature overnight, the reaction mixture is poured into 300 ml. of water to which is then added 250 ml. of chloroform. The pH of the aqueous layer is adjusted to 9.8 and the chloroform layer separated. The aqueous layer is extracted with chloroform again, and the chloroform extracts are combined, dried over sodium sulfate and concentrated to a white foam. The residual foam is dissolved in a stirring mixture of 125 ml. of water and 125 ml. of fresh chloroform and the pH adjusted to 4.9. The chloroform is separated and discarded, and the aqueous layer adjusted to pH 5, 6, 7 and 8, being extracted after each adjustment with fresh chloroform. The extracts from the aqueous at pH 6 and 7 are combined, washed with a saturated brine solution and dried over sodium sulfate. Removal of the solvent provides 1.72 g. of the desired product as a white foam. The product is dissolved in a minimal amount of diethyl ether and is subsequently treated with hexane to turbidity. The crystalline product which forms is filtered and dried, 1.33 g., m.p. 204.5°-206.5° C.

NMR (δ, CDCl₃): 3.31 (2H)s, 3.28 (1H)s, 2.31 (6H)s, 2.11 (3H)s and 1.5 (3H)s.

EXAMPLE 15

The procedure of Example 14 is repeated, starting with the appropriate 4''-deoxy-4''-oxo-erythromycin A and substituting isopropanol for methanol as the reaction solvent to give the following compounds:

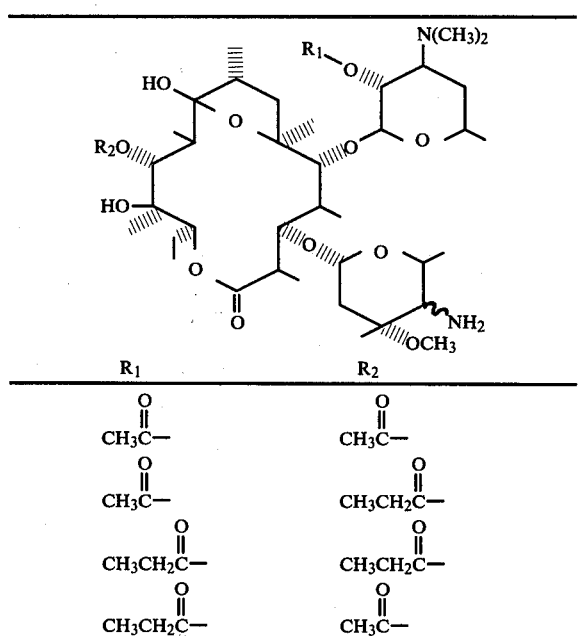

| R₁ | R₂ |
|---|---|
| $\underset{\text{CH}_3\text{C}-}{\overset{\text{O}}{\parallel}}$ | $\underset{\text{CH}_3\text{C}-}{\overset{\text{O}}{\parallel}}$ |
| $\underset{\text{CH}_3\text{C}-}{\overset{\text{O}}{\parallel}}$ | $\underset{\text{CH}_3\text{CH}_2\text{C}-}{\overset{\text{O}}{\parallel}}$ |
| $\underset{\text{CH}_3\text{CH}_2\text{C}-}{\overset{\text{O}}{\parallel}}$ | $\underset{\text{CH}_3\text{CH}_2\text{C}-}{\overset{\text{O}}{\parallel}}$ |
| $\underset{\text{CH}_3\text{CH}_2\text{C}-}{\overset{\text{O}}{\parallel}}$ | $\underset{\text{CH}_3\text{C}-}{\overset{\text{O}}{\parallel}}$ |

EXAMPLE 16

2'-Acetylerythromycin A 6,9-hemiketal 11,12-carbonate ester

To a solution of 13.2 g. of erythromycin A 6,9-hemiketal 11,12-carbonate ester (U.S. Pat. No. 3,417,077) in 150 ml. of benzene is added 1.8 ml. of acetic anhydride, and the reaction mixture allowed to stir at room temperature for 1.5 hrs. The solution is poured into 200 ml. of water and the aqueous phase basified to pH 9.0. The benzene layer is separated, dried over sodium sulfate and concentrated in vacuo to 15.3 g. of a white foam. On trituration with 50 ml. of diethyl ether the foam crystallizes. Filtration and drying of the product gives 12.6 g. of pure product, m.p. 224.5°-228.5° C.

NMR (δ, CDCl₃): 3.36 (3H)s, 2.30 (6H)s, 2.06 (3H)s and 1.61 (3H)s.

In a similar manner, by substituting an equivalent amount of propionic anhydride for acetic anhydride in the procedure of Example 16, 2'-propionylerythromycin A 6,9-hemiketal 11,12-carbonate ester is prepared.

EXAMPLE 17

2'-Acetyl-4''-deoxy-4''-oxo-erythromycin A 6,9-hemiketal 11,12-carbonate ester

To a suspension of 6.19 g. of N-chlorosuccinimide in 150 ml. of toluene and 50 ml. of benzene cooled to −5° C. is added 4.46 ml. of dimethylsulfide. After stirring for 20 min. the resulting suspension is cooled to −25° C. and 12.4 g. of 2'-acetylerythromycin A 6,9-hemiketal 11,12-carbonate ester, partially dissolved in 80 ml. of toluene, is added dropwise. The temperature, which is maintained between −19° to −25° C. during the addition, is kept at −25° C. for 2 hrs. At the end of this period 6.79 ml. of triethylamine is added all at once. The cooling bath is removed and the temperature allowed to rise to −10° C. The reaction mixture is then poured into water and the aqueous phase adjusted from 8.4 to 9.0. The organic layer is separated, dried over sodium sulfate and concentrated under vacuum to a white foam (14.0 g.). Trituration of the residue with diethyl ether causes the foam to crystallize. Filtration and drying of the product gives 11.3 g. of crystalline material, m.p. 212°–213.5° C.

NMR (δ, CDCl$_3$): 5.26 (1H)t, 3.36 (3H)s, 2.30 (6H)s, 2.13 (3H)s, 1.63 (3H)s and 1.50 (3H)s.

Similarly, 2′-propionyl-4″-deoxy-4″-oxo-erythromycin A 6,9-hemiketal 11,12-carbonate ester is prepared by the procedure of Example 17 by the replacement of the 2′-acetyl ester with an equivalent amount of 2′-propionylerythromycin A 6,9-hemiketal 11,12-carbonate ester.

EXAMPLE 18

4″-Deoxy-4″-oxo-erythromycin A 6,9-hemiketal 11,12-carbonate ester

Forty-two and nine-tenths grams of 2′-acetyl-4″-deoxy-4″-oxo-erythromycin A 6,9-hemiketal 11,12-carbonate ester is added to 800 ml. of methanol and the resulting solution allowed to stir at room temperature for 72 hrs. On removal of the solvent in vacuo there remains 41 g. of the product as a white foam. The residual material is dissolved in about 100 ml. of acetone followed by the careful addition of water to the precipitation point. The resulting crystalline solid is allowed to stir for 40 min., and this then filtered and dried to give 34.2 g. of desired product, m.p. 186.5°–188° C.

NMR (δ, CDCl$_3$): 5.66 (1H)t, 3.35 (3H)s, 2.35 (6H)s, 1.65 (3H)s and 1.51 (3H)s.

In a similar manner the same product is obtained when an equivalent amount of 2′-propionyl-4″-deoxy-4″-oxo-erythromycin A 6,9-hemiketal 11,12-carbonate ester is employed in the above procedure in place of the 2′-acetyl ester.

EXAMPLE 19

4″-Deoxy-4″-amino-erythromycin A 6,9-hemiketal 11,12-carbonate ester

To 189 g. of 4″-deoxy-4″-oxo-erythromycin A 6,9-hemiketal 11,12-carbonate ester in 1200 ml. of methanol at room temperature is added with stirring 193 g. of ammonium acetate. After 5 min. the resulting solution is cooled to about −5° C. and is subsequently treated with 13.4 g. of 85% sodium cyanoborohydride in 200 ml. of methanol over a 45 min. addition period. The cooling bath is removed and the reaction mixture allowed to stir at room temperature overnight. The reaction mixture is reduced in volume to 800 ml. in vacuo and added to a stirring mixture of 1800 ml. of water and 900 ml. of chloroform. The pH is adjusted from 6.2 to 4.3 with 6 N hydrochloric acid and the chloroform layer separated. The chloroform is combined with 1 l. of water and the pH adjusted to 9.5. The organic phase is separated, dried over sodium sulfate and concentrated under reduced pressure to give 174 g. of a white foam. The residual material is dissolved in a mixture of 1 l. of water and 500 ml. of ethyl acetate and the pH adjusted to 5.5. The ethyl acetate layer is separated and the aqueous layer adjusted to pH 5.7 and 9.5 successively, being extracted after each pH adjustment with 500 ml. of fresh ethyl acetate. The ethyl acetate extract at pH 9.5 is dried over sodium sulfate and concentrated in vacuo to dryness, 130 g. One-hundred and twenty grams of the residual foam is dissolved in a mixture of 1 l. of water and 1 l. of methylene chloride. The pH of the aqueous layer is adjusted to 4.4, 4.9 and 9.4 successively, being extracted after each adjustment with 1 l. of fresh methylene chloride. The methylene chloride extract at pH 9.4 is dried over sodium sulfate and concentrated under reduced pressure to give 32 g. of the product as a white foam. Crystallization from 250 ml. of acetone-water (1:1, v:v) gives 28.5 g. of the crystalline epimers.

NMR 100 Mz (δ, CDCl$_3$): 5.20 (1H)m, 3.37 (1.5H)s, 3.34 (1.5H)s, 2.36 (6H)s, 1.66 (3H)s and 1.41 (3H)s.

EXAMPLE 20

Separation of the Epimers of 4″-Deoxy-4″-amino-erythromycin A 6,9-hemiketal 11,12-carbonate Ester On to a high-pressure-liquid-chromatography column (⅜″×9 cm.) packed with Gf 254 silica gel impregnated with formamide and eluted with chloroform is applied 200 mg. A pressure of 240 p.s.i. is applied with a rate of 4.76 cc. per min. and a fraction size of 10 ml. is employed. Fractions 14 thru 21 and 24 thru 36 are collected.

Fractions 14 thru 21 are combined and concentrated to about 50 ml. Water (50 ml.) is added and the pH adjusted to 9.0. The chloroform layer is separated, dried over sodium sulfate and concentrated to give 106 mg. of a white foam. Trituration with diethyl ether causes the foam to crystallize. After stirring at room temperature for one hour the crystalline product is filtered and dried, 31.7 mg., m.p. 194°–196° C.

NMR 100 Mz (δ, CDCl$_3$): 5.24 (1H)d, 5.00 (1H)t, 3.40 (3H)s, 2.40 (6H)s, 1.66 (3H)s and 1.40 (3H)s.

Fractions 24 thru 36 are combined and worked up as above to give 47.1 mg. of product as a white foam, which is identical to the material from Example 25.

EXAMPLE 21

To a suspension of 11.1 g. of 2′-acetyl-4″-deoxy-4″-oxo-erythromycin A 6,9-hemiketal 11,12-carbonate ester in 300 ml. of isopropanol at room temperature is added with stirring 10.7 g. of ammonium acetate. After 5 min., 747 mg. of sodium cyanoborohydride in 130 ml. of isopropanol is added over a period of 30 min. and the resulting reaction mixture is allowed to stir at room temperature overnight. The pale yellow solution is poured into 1100 ml. of water to which is then added 400 ml. of diethyl ether. The pH is adjusted to 4.5 and the ether layer is separated. The aqueous layer is basified to pH 9.5 and extracted (2×500 ml.) with chloroform. The chloroform extracts are combined, dried over sodium sulfate and concentrated to give 7.5 g. of a yellow foam. Recrystallization of the residual material from diethyl ether gives 1.69 g. which is retained along with the mother liquors.

The mother liquor is treated with 75 ml. of water, and the pH adjusted to 5.0. The ether layer is replaced with 75 ml. of fresh ether and the pH adjusted to 5.4. The ether is replaced with ethyl acetate and the pH raised to 10. The basified aqueous layer is extracted (2×75 ml.) with ethyl acetate and the first ethyl acetate extract dried over sodium sulfate and concentrated to dryness. The residual foam (1.96 g.) is added to a mixture of 75 ml. of water and 50 ml. of diethyl ether and the pH adjusted to 5.05. The ether is separated and the aqueous layer adjusted successively to pH 5.4, 6.0, 7.05 and 8.0, being extracted after each pH adjustment with 50 ml. of fresh diethyl ether. The pH is finally adjusted to 9.7 and the aqueous layer extracted with 50 ml. of ethyl acetate. The ether extract carried out at pH 6.0 is combined with 75 ml. of water and the pH adjusted to 9.7. The ether layer is separated, dried and concentrated in vacuo to give 460 mg. of a white foam.

NMR 100 Mz ($\delta$, CDCl$_3$): 5.20 (1H)t, 3.43 (2H)s, 3.40 (1H)s, 2.38 (6H)s, 2.16 (3H)s, 1.70 (3H)s and 1.54 (3H).

The NMR data indicates the product to be the epimers of 2'-acetyl-4''-deoxy-4''-amino-erythromycin A 6,9-hemiketal 11,12-carbonate ester.

The 1.69 g. indicated above is dissolved in a mixture of 75 ml. of water and 75 ml. of diethyl ether and the pH adjusted to 4.7. The ether is separated and the aqueous layer further extracted with fresh ether (75 ml.) at pH 5.05 and 5.4, and with ethyl acetate (2×75 ml.) at pH 9.7. The combined ethyl acetate extracts are dried over sodium sulfate and concentrated under reduced pressure to give 1.26 g. of a white foam. Crystallization of this residual material gives 411 mg. of product, m.p. 193°–196° C. (dec.). The mother liquor is concentrated to dryness, and the residue dissolved in hot ethyl acetate. The solution is allowed to stand overnight at room temperature. The crystalline solids which precipitate are filtered and dried, 182 mg., m.p. 198°–202° C. (dec.) to give additional product.

NMR 100 Mz ($\delta$, CDCl$_3$): 5.10 (1H)t, 3.34 (2H)s, 3.30 (1H)s, 2.30 (6H)s, 2.08 (3H)s, 1.62 (3H)s and 1.48 (3H)s.

The NMR data indicates the product to be the epimers of 2'-acetyl-4''-deoxy-4''-amino-erythromycin A 11,12-carbonate ester.

In a similar manner, when Example 21 is repeated, starting with 2'-propionyl-4''-deoxy-4''-oxo-erythromycin A 6,9-hemiketal 11,12-carbonate ester, there is obtained 2'-propionyl-4''-deoxy-4''-amino-erythromycin A 6,9-hemiketal 11,12-carbonate ester and 2'-propionyl-4''-deoxy-4''-amino-erythromycin A 11,12-carbonate ester.

EXAMPLE 22

A solution of 400 mg. of 2'-acetyl-4''-deoxy-4''-amino-erythromycin A 6,9-hemiketal 11,12-carbonate ester in 20 ml. of methanol is allowed to stir overnight at room temperature. The reaction solution is poured into 100 ml. of water followed by the addition of 50 ml. of ethyl acetate. The pH is adjusted to 9.5 and the organic phase separated. The extraction is repeated again with 50 ml. of fresh ethyl acetate. The combined ethyl acetate extracts are dried over sodium sulfate and concentrated to give 392 mg. of a white foam. Trituration with diethyl ether and scratching with a glass rod affects crystallization. After standing at room temperature for 30 min., the crystalline solids are filtered and dried, 123 mg., and the mother liquor is retained. The product is identical by NMR to material prepared in Example 24.

NMR 100 Mz ($\delta$, CDCl$_3$): 3.26 (3H)s, 2.32 (6H)s, 1.61 (3H)s and 1.44 (3H)s.

The NMR data indicates that the crystalline product is a single epimer of 4''-deoxy-4''-amino-erythromycin A 11,12-carbonate ester.

The retained mother liquor is concentrated in vacuo to give 244 mg. of a white foam.

The product is identical with material from Example 19.

The NMR data indicates that this product is a mixture of the epimers of 4''-deoxy-4''-amino-erythromycin A 6,9-hemiketal 11,12-carbonate ester and identical with the product of Example 19.

EXAMPLE 23

In a manner similar to the procedure of Example 22, methanolysis of 2'-propionyl-4''-deoxy-4''-amino-erythromycin A 6,9-hemiketal 11,12-carbonate ester gives 4''-deoxy-4''-amino-erythromycin A 11,12-carbonate ester and 4''-deoxy-4''-amino-erythromycin A 6,9-hemiketal 11,12-carbonate ester.

EXAMPLE 24

Eight grams of the epimeric mixture of 4''-deoxy-4''-amino-erythromycin A 11,12-carbonate ester from the non-crystalline product of Example 19 is dissolved in 50 ml. of diethyl ether. The product is induced to crystallize by scratching with a glass rod. After 20 min. stirring, the crystalline product is filtered and dried, 1.91 g., m.p. 198.5°–200° C.

NMR 100 Mz ($\delta$, CDCl$_3$): 3.26 (3H)s, 2.30 (6H)s, 1.61 (3H)s and 1.45 (3H)s.

The NMR data indicates that the crystalline product is a single epimer of 4''-deoxy-4''-amino-erythromycin A 11,12-carbonate ester and identical with the ketone product from Example 22.

EXAMPLE b 25

One gram of the epimer of Example 24 is dissolved in 20 ml. of acetone and heated at steam bath temperatures until the boiling point is reached. Water (25 ml.) is added and the resulting solution allowed to stir at room temperature. After one hour of stirring, the precipitate which forms is filtered and dried to give 581 mg., m.p. 147°–149° C.

NMR 100 Mz ($\delta$, CDCl$_3$): 5.12 (1H)d, 3.30 (3H)s, 2.30 (6H)s, 1.62 (3H)s and 1.36 (3H)s.

The NMR data indicates the product to be a single epimer of 4''-deoxy-4''-amino-erythromycin A 6,9-hemiketal 11,12-carbonate ester and identical to the epimer in fractions 24–36 of Example 20.

EXAMPLE 26

4''-Deoxy-4''-Amino-Erythromycin A

Twenty grams of 4''-deoxy-4''-oxo-erythromycin A, 31.6 g. of ammonium acetate and 10 g. of 10% palladium-on-charcoal in 200 ml. of methanol is shaken at ambient temperatures in a hydrogen atmosphere at an initial pressure of 50 p.s.i. overnight. The spent catalyst is filtered and the filtrate concentrated to dryness in vacuo. The residue is partitioned between water-chloroform at a pH of 5.5. The aqueous layer is separated, the pH adjusted to 9.6 and chloroform added. The organic layer is separated, dried over sodium sulfate and concentrated under reduced pressure to dryness. The residual white foam (19 g.) is triturated with 150 ml. of diethyl ether at room temperature for 30 minutes. The resulting solids are filtered and dried to give 9.45 g. of a single epimer indistinguishable from that in Example 10.

The diethyl ether filtrate is concentrated to dryness to give 6.89 g. of product consisting of the other epimer plus some impurities.

EXAMPLE 27

4"-Deoxy-4"-Amino-Erythromycin A

Two grams of 4"-deoxy-4"-oxo-erythromycin A, 3.1 g. of ammonium acetate and 2.0 g. of Raney nickel in 50 ml. of methanol is shaken at room temperature in a hydrogen atmosphere at an initial pressure of 50 p.s.i. overnight. An additional 3.16 g. of ammonium acetate and 2.0 g. of Raney nickel are added and the hydrogenation continued for an additional 5 hours. The solids are filtered and the filtrate concentrated to dryness in vacuo. The residue is added with stirring to a mixture of water-chloroform, and the pH adjusted from 6.4 to 5.5. The aqueous phase is separated, the pH adjusted to 9.6 and fresh chloroform added. The chloroform extract is separated, dried over sodium sulfate and concentrated under reduced pressure to give 1.02 g. of the product as a yellow foam. The predominant isomer has the opposite configuration at 4" as the compound of Example 10.

EXAMPLE 28

2'-Acetyl-4"-deoxy-4"-amino-erythromycin B

To a solution of 4.5 g. of 2'-acetyl-4"-deoxy-4"-oxo-erythromycin B (U.S. Pat. No. 3,884,903) in 45 ml. of isopropanol under a nitrogen atmosphere is added with stirring 4.66 g. of dry ammonium acetate. After 10 min. 376 mg. of sodium cyanoborohydride is washed into the reaction mixture with 10 ml. of isopropanol and the reaction allowed to stir at room temperature overnight. The light yellow solution is poured into 400 ml. of water and the pH adjusted to 6.0. The aqueous is extracted at pH 6, 7, 7.5, 8, 9 and 10 using 250 ml. of diethyl ether for each extraction. The extracts at pH 8, 9 and 10 are combined and washed with 250 ml. of fresh water. The separated aqueous layer is extracted with ether (1×100 ml.) at pH 7, ethyl acetate (1×100 ml.) at pH 7, ether (1×100 ml.) at pH 7.5, ethyl acetate (1×100 ml.) at pH 7.5 and ethyl acetate (1×100 ml.) at pH 8, 9 and 10. The ethyl acetate extracts at pH 9 and 10 are combined, washed with a saturated brine solution and dried over sodium sulfate. Removal of the solvent in vacuo gives an epimeric mixture of the desired product as a cream colored foam.

In a similar manner, 4"-deoxy-4"-amino-erythromycin B is prepared from 4"-deoxy-4"-oxo-erythromycin B.

EXAMPLE 29

4"-Deoxy-4"-amino-erythromycin B

A solution of 4.34 g. of 2'-acetyl-4"-deoxy-4"-amino-erythromycin B in 100 ml. of methanol is allowed to stir at room temperature overnight. The solvent is removed under reduced pressure and the residual foam treated with a mixture of 100 ml. of chloroform and 100 ml. of water. The pH of the aqueous layer is adjusted to 9.5 and the organic layer separated. The chloroform layer is treated with fresh water and the pH adjusted to 4.0. The pH of the acid aqueous layer containing the product is gradually adjusted to 5, 6, 7, 8 and 9 by the addition of base, being extracted at each pH with fresh chloroform. The extracts at pH 6 and 7 contain the major portion of the product and these are combined and treated with fresh water at pH 4. The aqueous layer is again adjusted through pH 5, 6 and 7, being extracted at each pH with fresh chloroform. The chloroform extract at pH 6 is dried over sodium sulfate and concentrated to give the product as an epimeric mixture.

EXAMPLE 30

4"-Deoxy-4"-amino-erythromycin A 6,9-hemiketal 11,12-carbonate ester aspartate To a solution of 1.0 g. of 4"-deoxy-4"-amino-erythromycin A 6,9-hemiketal 11,12-carbonate ester in 6 ml. of acetone warmed to 40° C. is added 20 ml. of water followed by 175 mg. of L-aspartic acid. The mixture is heated to reflux for 1.5 hours and is then filtered while hot. The filtrate is concentrated by removal of the acetone and is subsequently freeze-dried to give 1.1 g. of the desired product as a white solid.

EXAMPLE 31

4"-Deoxy-4"-amino-erythromycin A 6,9-hemiketal 11,12-carbonate ester dihydrochloride To 7.58 g. of 4"-deoxy-4"-amino-erythromycin A 6,9-hemiketal 11,12-carbonate ester in 50 ml. of dry ethyl acetate is added 20 ml. of a 1 N ethyl acetate solution of hydrogen chloride, and the resulting solution concentrated to dryness under reduced pressure. The residual material is triturated with ether and filtered to give the desired salt.

By a similar procedure the amine compounds of the present invention are converted to their di-acid addition salts.

EXAMPLE 32

4"-Deoxy-4"-amino-erythromycin A 6,9-hemiketal 11,12-carbonate ester hydrochloride The procedure of Example 31 is repeated with the exception that 10 ml. of a 1 N ethyl acetate solution of hydrogen chloride is added. The solution is concentrated to dryness in vacuo and the residual mono-hydrochloride salt is triturated with ether and filtered.

By a similar procedure the amine compounds of the present invention are converted to their mono-acid addition salts.

What is claimed is:

1. A compound selected from the group consisting of:

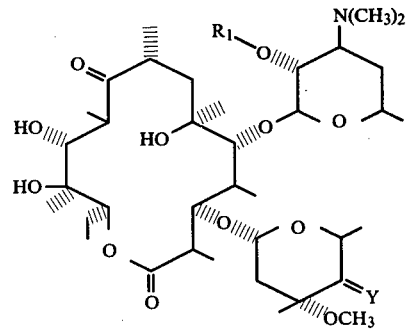

I and

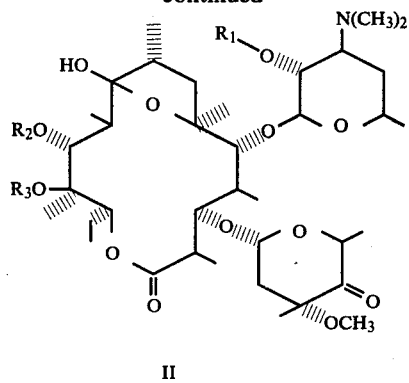

II wherein $R_1$ is selected from the group consisting of hydrogen and alkanoyl having from two to three carbon atoms; $R_2$ is alkanoyl having two to three carbon atoms; Y is selected from the group consisting of N—OH and

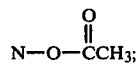

$R_3$ is hydrogen; and $R_2$ and $R_3$ when taken together are

2. A compound of claim 1, Formula I, wherein $R_1$ is selected from the group consisting of hydrogen and acetyl.

3. The compound of the formula:

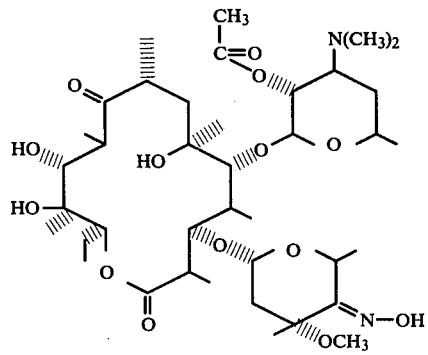

4. The compound of the formula:

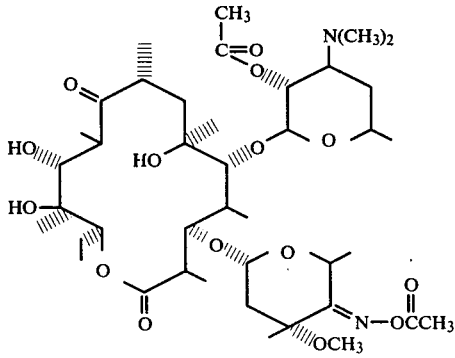

5. The compound of the formula:

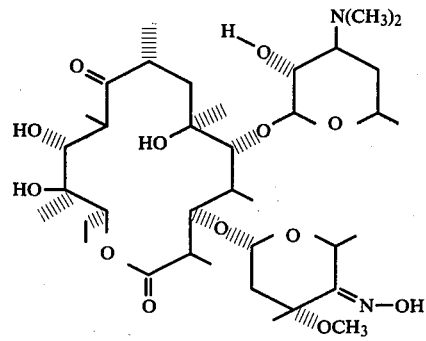

6. The compound of the formula:

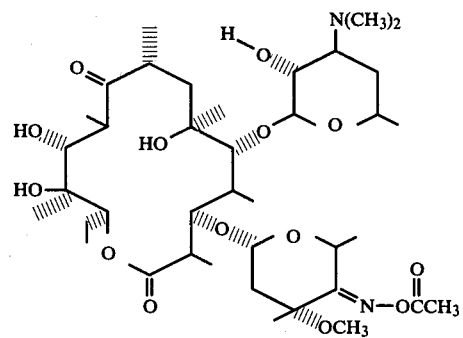

7. The compound of claim 1, Formula II, wherein $R_1$ is selected from the group consisting of hydrogen and acetyl.

8. The compound of the formula:

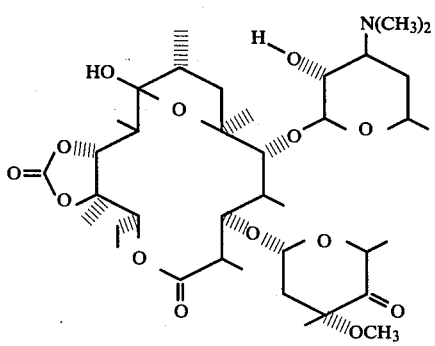

9. The compound of the formula:

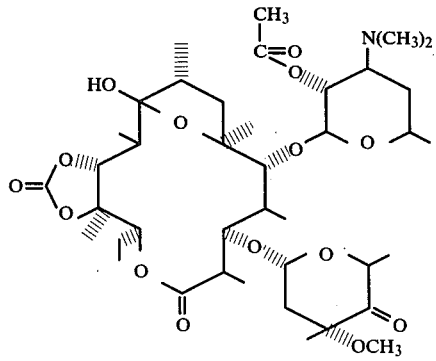

10. A 4''-amino epimeric compound selected from the group consisting of:

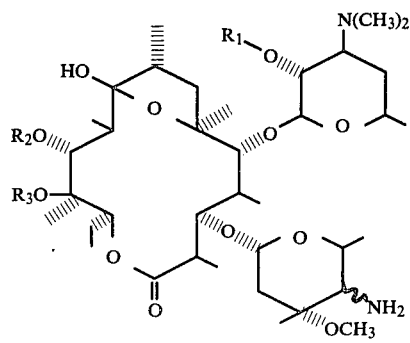  III and

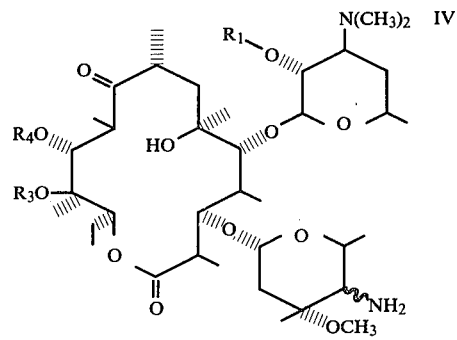  IV and a pharmaceutically acceptable acid addition salt thereof wherein $R_1$ and $R_4$ are each selected from the group consisting of hydrogen and alkanoyl having from two to three carbon atoms; $R_2$ is alkanoyl having from two to three carbon atoms; $R_3$ is hydrogen; $R_2$ and $R_3$ when taken together are

;

and $R_3$ and $R_4$ when taken together are

.

11. A compound of claim 10, Formula III, wherein $R_2$ and $R_3$ when taken together are

.

12. The compound of the formula:

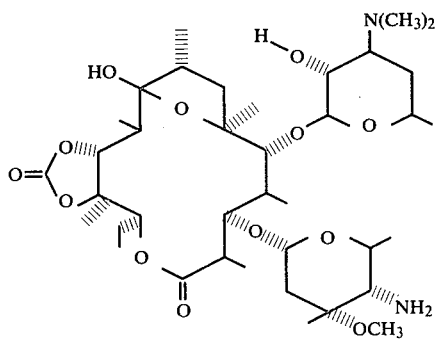

13. The compound of the formula:

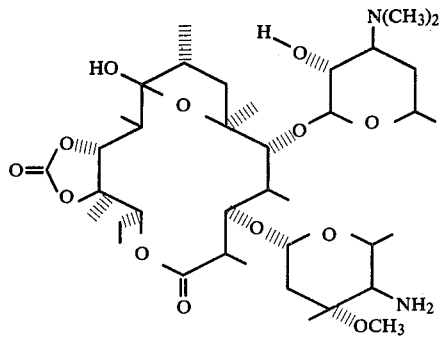

14. A compound of claim 10, Formula IV, wherein $R_4$ is hydrogen.

15. The compound of the formula:

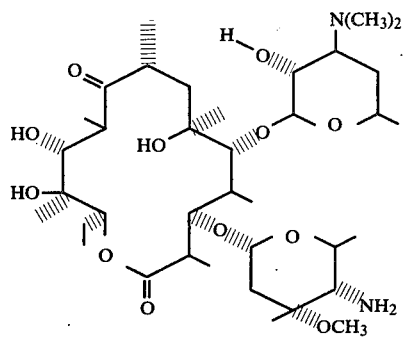

16. The compound of the formula:

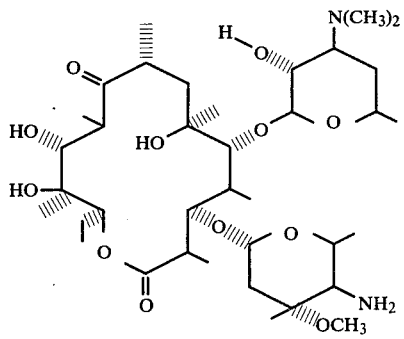

17. A compound of claim 10, Formula IV, wherein $R_3$ and $R_4$ when taken together are

.

18. The compound of the formula:

19. The compound of the formula:
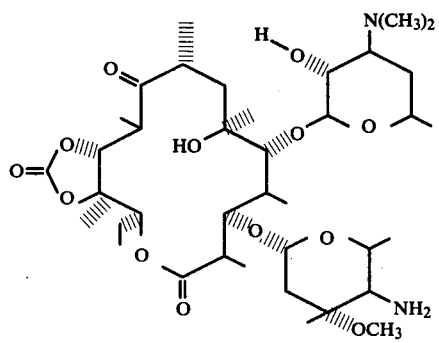
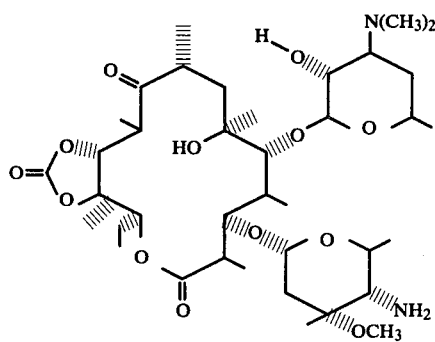
* * * * *